United States Patent [19]

Anan et al.

[11] Patent Number: 5,686,981
[45] Date of Patent: Nov. 11, 1997

[54] OPHTHALMOLOGIC DEVICE FOR ACCURATELY POSITIONING A CONTACT LENS TO AN EYE

[75] Inventors: Naoki Anan, Seki; Tadashi Sawano, Nagoya; Hiroyuki Ohyama; Shingo Hibino, both of Seki, all of Japan

[73] Assignee: Menicon Co., Ltd, Nagoya, Japan

[21] Appl. No.: 537,768
[22] PCT Filed: Feb. 22, 1995
[86] PCT No.: PCT/JP95/00258
 § 371 Date: Oct. 20, 1995
 § 102(e) Date: Oct. 20, 1995
[87] PCT Pub. No.: WO95/22926
 PCT Pub. Date: Aug. 31, 1995

[30] Foreign Application Priority Data

Feb. 28, 1994 [JP] Japan ................... 6-029938

[51] Int. Cl.⁶ ................ A61B 3/10; A61B 3/00; A61B 3/14
[52] U.S. Cl. ............. 351/212; 351/247; 351/206
[58] Field of Search ............... 351/205, 206, 351/212, 247; 354/62

[56] References Cited

U.S. PATENT DOCUMENTS 5,293,533  3/1994  Klyce .................... 351/212

FOREIGN PATENT DOCUMENTS 54-158093  12/1979  Japan.
4-200524   7/1992   Japan.
6-45998    2/1994   Japan.

*Primary Examiner*—Huy Mai
*Attorney, Agent, or Firm*—Armstrong, Westerman, Hattori, McLeland & Naughton

[57] ABSTRACT

A device of the present invention includes: apparatus for photographing an anterior eye segment of a subject; a first display device for displaying an image of the anterior eye segment; a device for processing the displayed image to detect the relative positions of a pupil and a contact lens, respectively; a calculating apparatus for obtaining the relationship of relative positions between them by calculating; and a second display device for displaying the obtained relationship of the relative positions. The described arrangement is particularly useful for inspecting a condition for the putting on of the contact lens by measuring the relationship of the relative positions between the contact lens at the time of being put on and the pupil of the concerned eye segment.

9 Claims, 7 Drawing Sheets

OPHTHALMOLOGIC DEVICE FOR ACCURATELY POSITIONING A CONTACT LENS TO AN EYE

TECHNICAL FIELD

The present invention relates to a measuring and inspecting device for ophthalmologic use which inspects the condition of an eye of a person for fitting a contact lens. More particularly, it relates to a measuring and inspecting device for ophthalmologic use which inspects the relationship of relative positions between a contact lens being put on and a pupil which receives the contact lens.

BACKGROUND ART

Conventionally, the relationship of relative positions between a contact lens and a pupil has been decided by an inspector's subjectivity while utilizing a slit lamp biomicroscope. Therefore, it is difficult to measure the relationship of positions quantitatively, and there have not been developed any devices especially adapted to perform this function.

On the other hand, contact lenses exist in which the thereof is not a uniform spherical surface but is, instead, an aspherical surface, such as an elliptic surface, for the purpose of improving the case of installing or the optical effect of the contact lens. When such contact lens is put on, it is necessary to make a visual axis, that is by line of sight a center position of a pupil, correspond with an optical axis of the contact lens so as to obtain adequate fitting of the contact lens. However, as mentioned above, the relationship of the positions between the pupil and the contact lens has been conventionally determined by relying upon the inspector's subjectivity, thereby, there have been some cases wherein correct prescription, that is, prescription with correct determination of the relationship of positions between the visual axis and optical axis, cannot be made.

Further, when a special lens, such as a bifocal contact lens, as shown in FIG. 4 (a contact lens having two kinds of refractive power), a multifocal contact lens (a contact lens having many kinds of refractive power), and a toric contact lens (a contact lens whose refractive power varies along the circumferencial direction at an interval of $\pi$) is put on, precise measurement cannot be done, although the visual axis and the optical axis of the contact lens have to be considered strictly.

The present invention has been made to solve such problem in the conventional method for deciding the relationship of relative positions between the pupil (visual axis) and the contact lens, and it is, therefore, an object of the present invention to provide a device capable of measuring the relationship of the positions quantitatively and precisely to enable correct prescription of the contact lens easily and based on the an objective decision.

DISCLOSURE OF THE INVENTION

A measuring and inspecting device for ophthalmologic use of the present invention comprises: a photographing means for photographing an anterior eye segment of a subject (a person to be examined); a first display means for displaying an image of the anterior eye segment of the subject photographed by the photographing means; a first position-detecting means for processing the image of the anterior eye segment to detect a position of a pupil; a second position-detecting means for detecting a position of a contact lens put on the subject being tested a calculating the means for calculating relationship of relative positions between the pupil and the contact lens based on positions of the pupil and the contact lens detected by the first position-detecting means and the second position-detecting means; and a second display means for displaying the relationship of the relative positions calculated by the calculating means.

Furthermore, it is preferable that the device further includes an illuminating means for illuminating the anterior eye segment of the subject in order to make the outer condition of the eye constant for measuring.

Further, it is preferable that the illuminating means is variable in illuminance in order to enable measurement in which various conditions (i.e. each of the lighting condition of inside of a room, out of doors, lighting at night, or the like) are assumed.

Further, it is preferable that an illuminance measuring means is provided, since lightness can be determined quantitatively, and more precise measurement of a diameter of the pupil can be made.

Moreover, it is preferable that the first display means and the second display means are provided in the same display device, since an inspector can recognize a condition of the image of the anterior eye segment and the relationship of the position thereof by comparing them to each other, and space reduction of the device can be achieved.

Further, it is preferable that the second display means is provided with a printer means in order that measured information can be recorded on paper.

According to the present invention, the image of the anterior eye segment of a subject which has been photographed by the photographing means is displayed by the first display means, and the image of the anterior eye segment is processed with the first position-detecting means, so that the position of the pupil is detected. Further, by utilizing the second position detecting means, the position of the contact lens put on by the subject is detected. Next, the relationship of relative positions between the pupil and the contact lens detected by the first detecting means and second detecting means is calculated by the calculating means, and this relationship of relative positions is displayed by the second display means, whereby the relationship of relative positions can be determined quantitatively. Moreover, a rotational angle and a displacement, or the like, of the contact lens can be calculated quantitatively, which enables easy confirmation of the putting-on condition of the contact lens or determination of the prescription.

Further, by combination with the described illuminating means, measurement under a constant condition or various illumination conditions is also made possible. Still further, for a contact lens which requires an analysis on a complicated use condition, for example, a contact lens like a bifocal contact lens in which the pupil is covered by a plurality of optical power regions, effective measurement can be made.

BEST MODE FOR CARRYING OUT THE INVENTION

Figure 1:
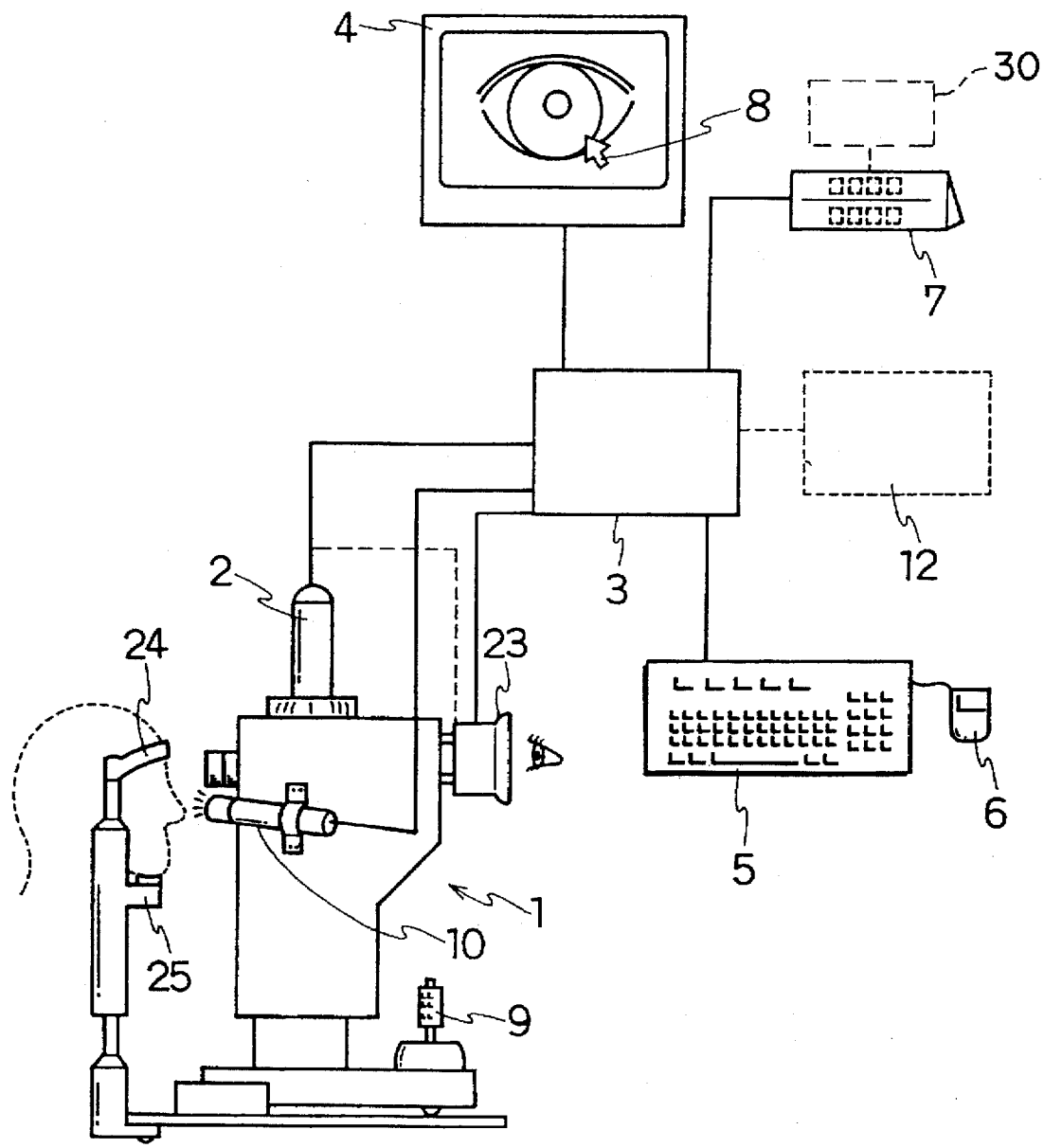
FIG. 1 is a schematic explanatory view showing an embodiment of a measuring and inspecting device for ophthalmologic use of the present invention.
Figure 2:
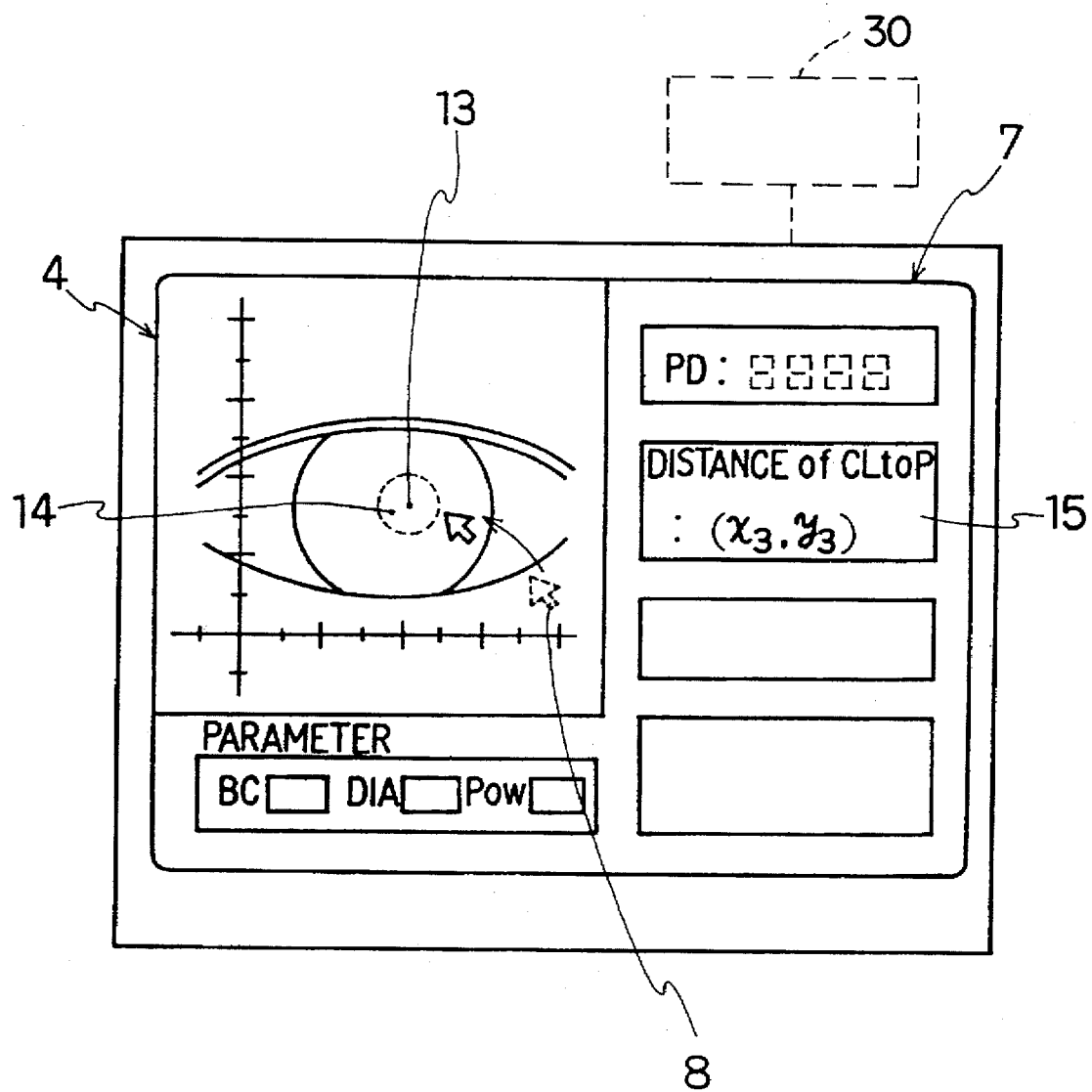
FIG. 2 is a schematic explanatory view showing another embodiment of a display means portion of the measuring and inspecting device for ophthalmologic use of the present invention.
Figure 3A:
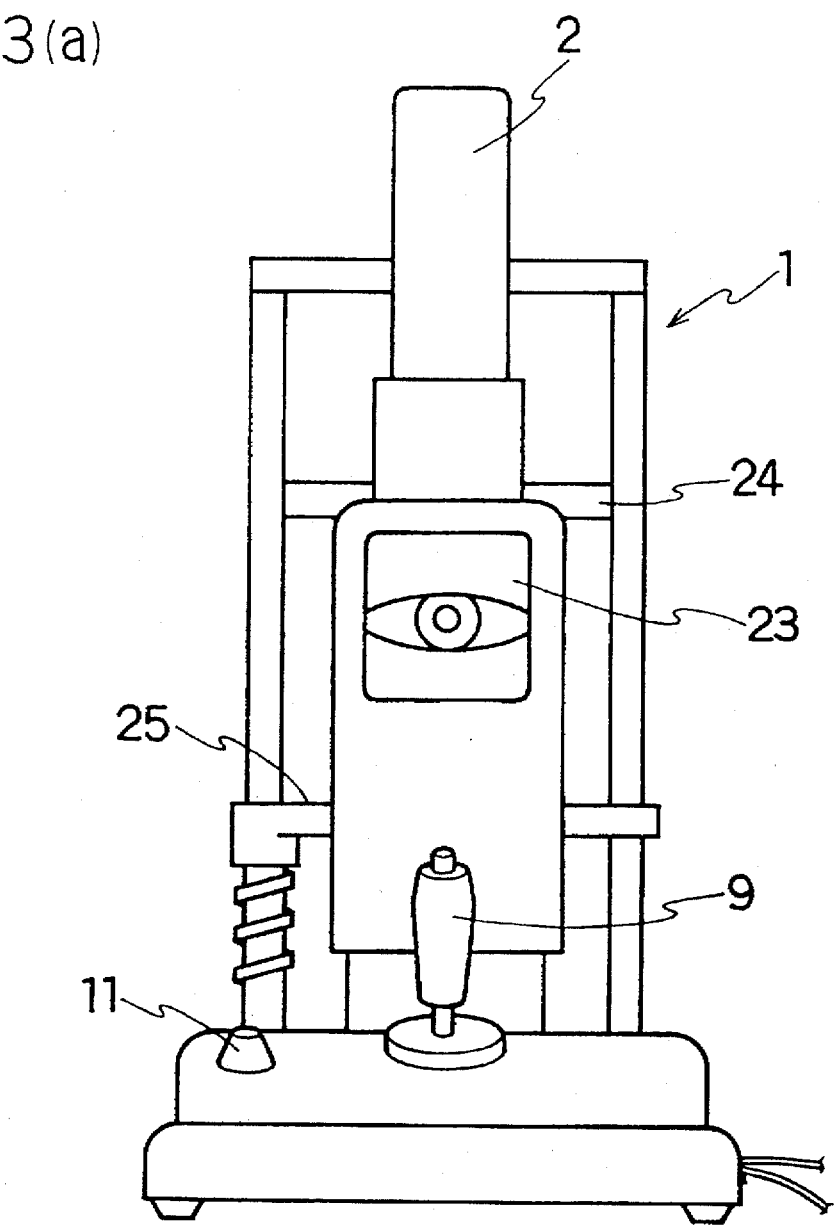
FIG. 3 is a schematic explanatory view showing another embodiment of an observing device portion of the measuring and inspecting device for ophthalmologic use of the present invention.
Figure 3B:
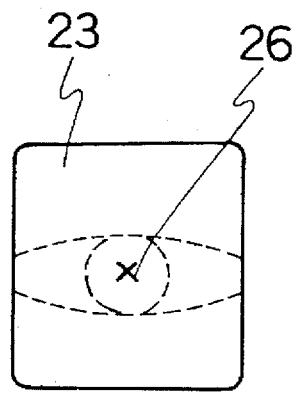

Next, an embodiment of a measuring and inspecting device for ophthalmologic use of the present invention will be explained in detail referring to the drawings. FIG. 1 is a schematic explanatory view of a measuring and inspecting device for ophthalmologic use of the present invention. In FIG. 1, numeral 1 denotes an observing device for observing an anterior eye segment. This device, to be more specific, has substantially the same basic function as that of a conventional slit lamp biomicroscope, that is, the device is so constituted that an inspector can observe an anterior eye segment of a subject whose chin is mounted on a chin rest 25 and whose forehead is applied to a forehead rest 24. In the present embodiment, the anterior eye segment of the subject is displayed on a television monitor 23, to allow the inspector to observe the anterior eye segment. That is, as shown in FIG. 3(a), an image of photographed anterior eye segment is provided on a side which the inspector observes by the television monitor 23, or the like, so that the inspector is not required to move his face to eyepieces for comparison by the slit lamp biomicroscope, thereby operational efficiency is improved. Furthermore, as shown in FIG. 3(b), a mark 26 is disposed at the center portion of the television monitor 23. This is a target for making a visual axis of a subject correspond with an optical of an optical system for photographing. An image of the anterior eye segment is moved by an operation bar 9 to position a center of a pupil at a position of the mark 26, thereby, the anterior eye segment can be effectively prevented from being photographed obliquely. In the present embodiment, the above-mentioned observing device 1 in which the inspector does not need to look into the eyepieces directly is employed, but an observing device of a type in which the inspector looks in, such eyepieces can, of course, also be employed. Numeral 2 denotes a photographing means provided on the observing device 1. For this, a CCD camera is used in the present embodiment, however, any photographing means can be employed as long as it can provide a photographed image for the television monitor. Numeral 3 is a calculating (processing) means for signal-processing an image photographed by the photographing means 2. Numeral 4 denotes a first display means, and as shown in the figures, a television monitor for displaying the anterior eye segment of a subject, or the like, can be used. Numeral 5 denotes an operating board (key board), and numeral 6 denotes a mouse. By these elements, to be specific, the device is so designed to enable the following operation. (1) A point to be measured in the image of the anterior eye segment displayed on the displaying screen shown in FIG. 2, is pointed at by the movement of the cursor 8. (2) An instruction to make the image of the anterior eye segment displayed on the above two monitors (that is, the first displaying means 4 and/or the television monitor 23) a standstill picture or a moving picture is made. (3) An instruction of regulating illuminance of the light for illuminating the anterior eye segment is made. (4) An instruction to enlarge or contract the image of the anterior eye segment displayed on the above two monitors is made.

In the present embodiment, as the first position-detecting means and/or second position-detecting means, there is employed means for processing a point to be measured in coordinate information, the point being pointed to on the screen through the operating board 5 or mouse 6. For example, various means such as means for position-detecting by recognizing figures in the device automatically after reading the image and means for directly pointing to a point on the screen on which the image is displayed by means of a pen, or the like, are employable.

Thus, the calculating means for calculating and processing the desired position detected by the first position-detecting means and the second position-detecting means is, in this embodiment, installed in the aforesaid calculating (processing) means 3. For example, with respect to each position of a pupil center $(x_1, y_1)$ detected by the first position-detecting means and a contact lens center $(x_2, y_2)$ detected by the second position-detecting means, the relationship of relative positions therebetween is obtained by the following calculation:

$$(x_3, y_3) = (x_2 - x_1, y_2 - y_1)$$

Numeral 7 denotes a second display means, which is a digital display device for displaying the relationship of relative positions between the contact lens and the pupil calculated by the calculating means. Furthermore, if the first display means 4 and the second display means 7 are provided on the same television monitor as shown in FIG. 2, the inspector can preferably make a condition of the image of the anterior eye segment correspond with the position of the image. On the display means of FIG. 2, in addition to a diameter of the pupil and the relationship of the relative positions 15 between the pupil center 13 and center of the contact lens 14, other desired data (a name of a subject, recognition of left and right eyes, an area of the pupil, a displacement of the contact lens and so on) can be displayed.

Furthermore, in the described embodiment, as the second display means 7, the digital display means or television monitor is shown as an example. A printer means, such as a printer device 30 capable of monochrome or color printing might be, however, attached to the second display means 7. Similarly, a printer means might be attached to the display means shown in FIG. 2 so as to enable printing of the image displayed on the display means. In these cases, information, such as the relationship of relative positions obtained by measurement can be outputted in the form of a paper.

Each example of a method for using the measuring and inspecting device and a procedure for operating it will now be described below.

(1) A subject who bears on its eye a contact lens for fitting purposes is positioned at a predetermined position of the observing device.

(2) An inspector positions the observing device 1 with the use of the operation bar 9 so as to make an eye to be inspected come to a correct position, that is, come to a position where photographing the eye can be done. The observing device might accommodate therein, a fixation light for maintaining a fixed position of the subject eye, thereby, the positioning can be done easily, and measurement and inspection succeeding to the positioning of the contact lens can be done more accurately.

(3) When photographing has become possible, for the purpose of entering a step for detecting the relationship of relative positions between the pupil of the subject and the contact lens, at first, the operation board is used to pose the image of the anterior eye segment displayed on the first display means.

(4) The mouse 6 additionally disposed at the operation board 5 is used to detect the position of the pupil of the image of the anterior eye segment displayed on the first display means and the position of the contact lens.

To be specific, at first, the operation board 5 is used to transmit a command of starting the work of detecting the position of the pupil to the calculating (processing) device 3, and to start a calculating (processing) program of the first position-detecting means for detecting the position of the pupil, thereby the position of the pupil is detected. Furthermore, in the present embodiment, the pupil is assumed to be an approximate circle, and an arbitrary three points on the outer periphery portion of the pupil is established by the mouse to detect the center position thereof.

Figure 5:
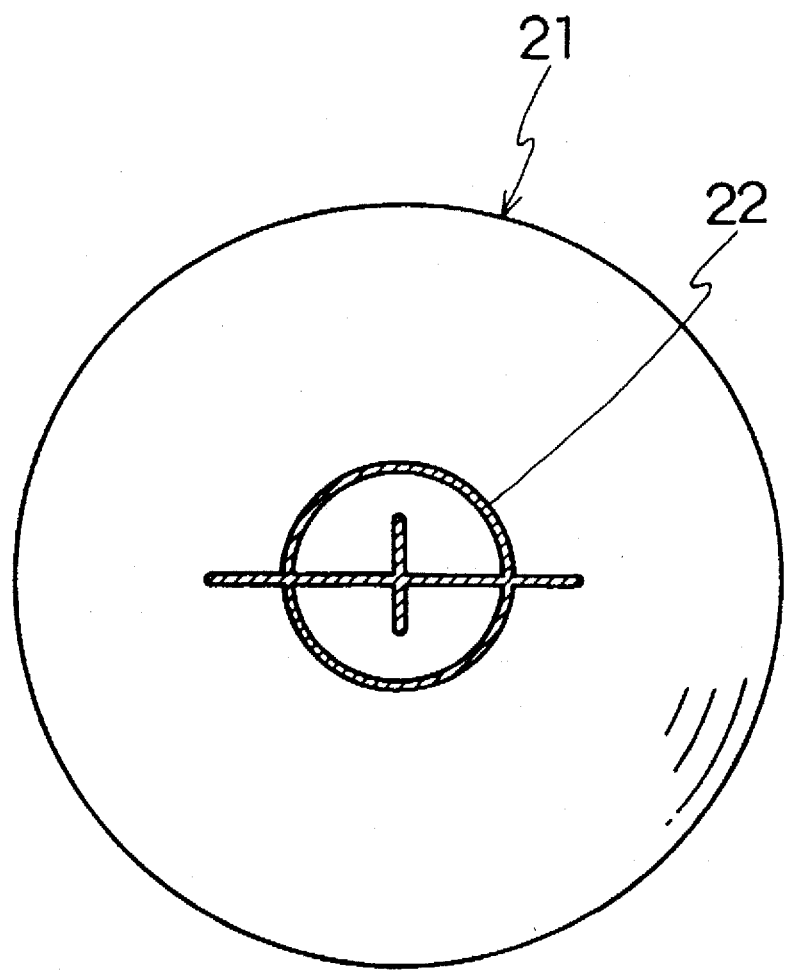
FIG. 5 is an explanatory view showing another embodiment of a contact lens in which effects of the measuring and inspecting device for ophthalmologic use of the present invention are evident.

Next, with respect to the position of the contact lens, the operation board 5 is similarly used to transmit a command of starting the work of detecting the position of the contact lens to the calculating (processing) device 3, and to start a calculating (processing) program of the second position-detecting means for detecting the position of the contact lens, thereby the position of the contact lens is detected. Furthermore, with respect to the position of the contact lens, it is considered that the three points of the outer periphery portion are established to detect the center of the contact lens. However, a contact lens 21 having a mark 22 which has previously been formed at the center portion thereof, as shown in FIG. 5, might alternatively be used. This contact lens 21 with the mark 22 is one which is used for a trial (or for testing purposes), and at least a shape of the posterior surface of the lens is so formed as to correspond to that of a contact lens which is actually being installed (or will be installed) on the subject. By the use of such contact lens for a trial, calculation of the relative position to the pupil can be performed much easier. Especially, in the case of a soft contact lens, the outer diameter thereof is generally large (about 11 to 14 mm) so that the soft contact lens, when worn, is partially covered by an eyelid, thereby determination of a point on the outer periphery portion becomes difficult. Therefore, it is very effective to form a mark at the center portion. Furthermore, when forming a mark, like the contact lens of FIG. 5, there is no problem in making the center position of the mark correspond with a center (i.e. the geometric center) of an outer edge of a contact lens, as shown in FIG. 5. However, if an optical center of a contact lens is designed not to correspond with its geometric center, it is more preferably that the mark is correspondingly formed at the optical center. Moreover, there is no particular limitation with respect to design of the mark, however, such a technique as disclosed in Japanese Unexamined Utility Model publication No. 96532/1988 (that is, a technique for disposing a character and/or a symbol (for example, a character, number, arrow mark, or the like) at the center portion of the contact lens) can be effectively used.

(5) The detected position of the pupil and the position of the contact lens are calculated and processed by the calculating means to calculate the relationship of relative positions.

(6) The relationship of relative positions obtained by calculation is displayed on the second display means.

Further, in the present embodiment, an illuminating means 10 is attached to a side surface of the observing means 1. Thereby, it is possible to illuminate the anterior segment of the eye to quantitatively determine a magnitude of a pupil diameter at illuminance at the time of measuring. Such illuminating means 10 might alternatively be accommodated in the observing device 10. Further, when the illuminating means can adjust illuminance, pupil diameters of a subject at different illuminances can be determined. Moreover, in the present embodiment, the same mouse is used for both the first and second position-detecting means to decide each position on the first display means (detected by the mouse). The present invention is not, however, limited to this, and the positions might be decided respectively by different means. For example, in the first position-detecting means, the keyboard of the operation board might be operated to decide the position of the pupil, while in the second position-detecting means, the mouse might be used to decide the position of the contact lens.

Figure 4:
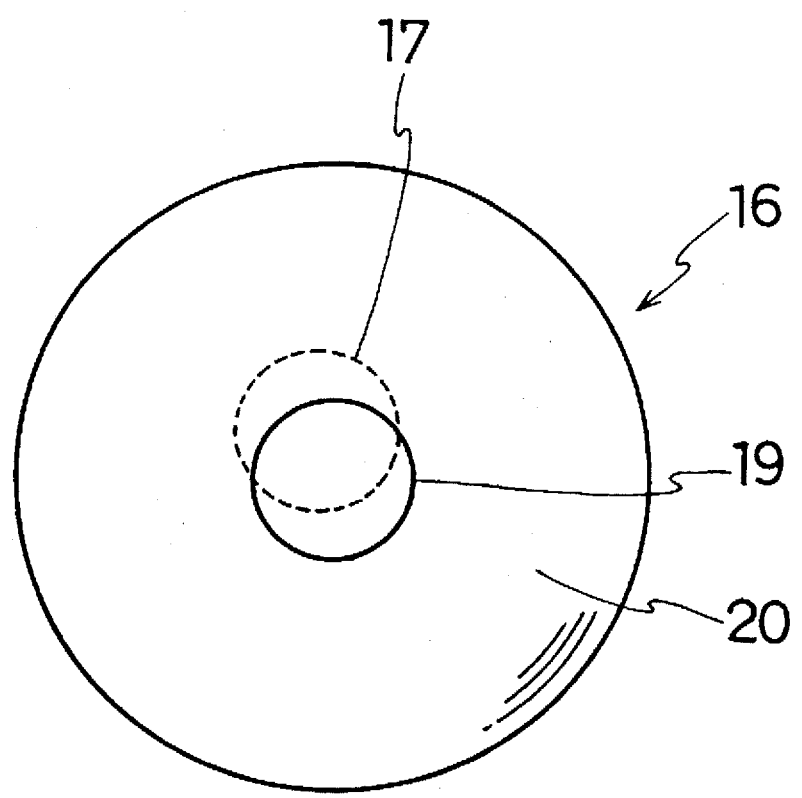
FIG. 4 is an explanatory view showing an embodiment of a contact lens in which effects of the measuring and inspecting device for ophthalmologic use of the present invention are evident.
Figure 7:
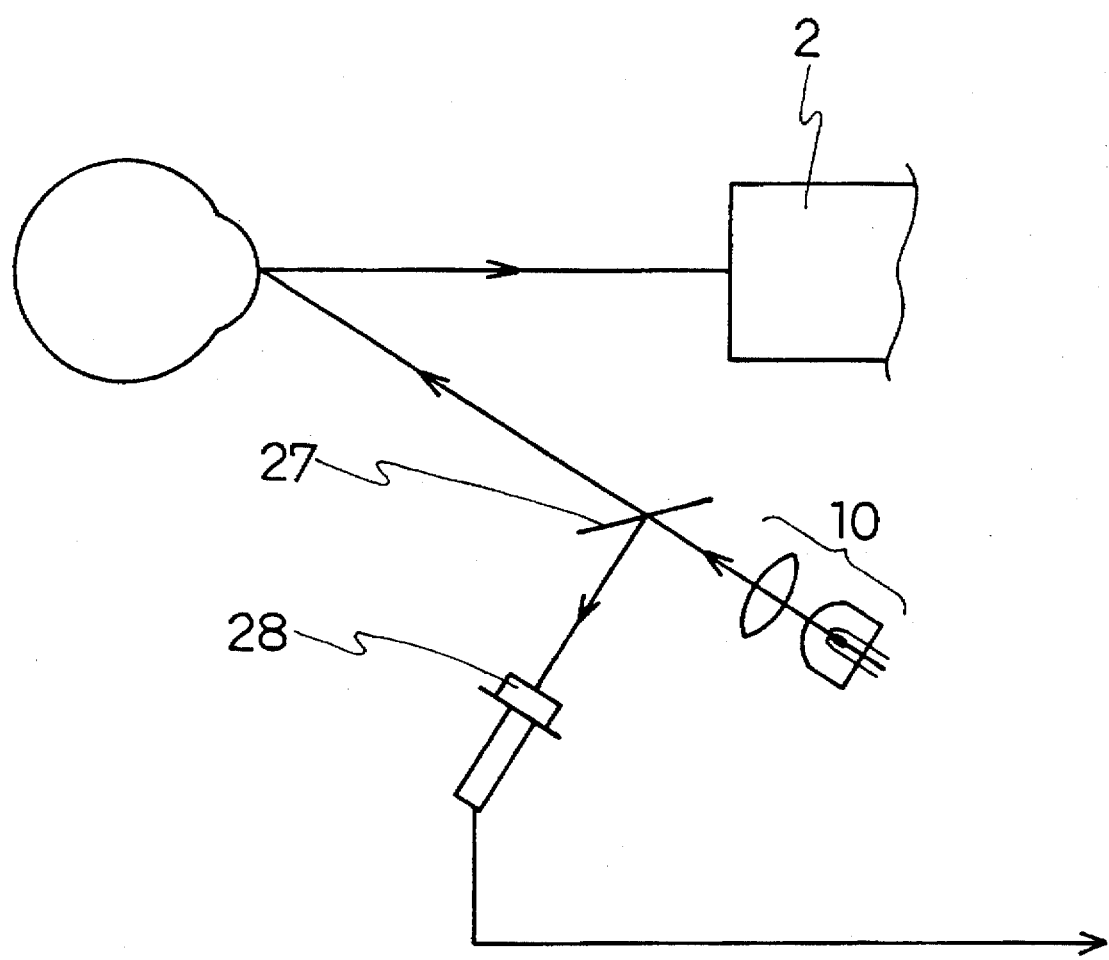
FIG. 7 is a schematic explanatory view showing an illuminance measuring means in a further embodiment of the measuring and inspecting device for ophthalmologic use of the present invention.

Further, as shown in FIG. 7, if there is employed a device wherein a half mirror is disposed on a light path of illumination, illuminance of an illuminating light is measured by an illuminance measuring means 28, and the measured value is simultaneously displayed on the first display means 4, the television monitor 23 or the like, through the calculating (processing) means 3, it is possible to determine illuminance quantitatively and to determine a pupil diameter more accurately. Especially, a very effective measured value can be obtained when selecting a bifocal contact lens 16, as shown in FIG. 4. The bifocal contact lens 16 has an optical zone for a near vision correction 19 at the center portion thereof and an optical zone for a far vision correction 20 at the peripheral portion thereof. It is judged, where each vision area is positioned in the pupil 17 and what degree the area occupies at different illuminance, thereby, it becomes possible to provide a subject with more suitable contact lens. Furthermore, the overlapped region of a vision area and a pupil can be easily obtained by obtaining the diameter of the pupil simultaneously when obtaining the position of the pupil as described above, by obtaining similarly the shape of the one optical zone of the contact lens, and, thereafter, by calculating and processing. Further, it is, of course, possible to make the calculating (processing) device 3 memorise a calculating and processing function like this in advance. Furthermore, the method of obtaining the area is not necessarily limited to a case where an optical zone is circular as shown in FIG. 4. It is possible to apply the method to optical zones with various shapes by utilizing the first position-detecting means and the second position-detecting means and to add a desired calculating and processing command (program) to a calculating (processing) device.

Operation of changing illuminance might be designed to be carried out by the operation board 5 shown in FIG. 1 or it might be designed to be carried by a dial-like regulating means 11 attached to the photographing means as shown in FIG. 3.

Moreover, in the case of a device having an illuminance measuring means 28 for measuring illuminance (referred to FIG. 7), by feeding back the measured result to the calculating (processing) device 3, the illuminance might be kept changing automatically until it reaches the illuminance set by the operation board. As the illumination measuring means 28, for example, a light meter available in the market which is equipped with a light-receiving sensor, an operation amplifier, and the like, can be employed.

In the embodiment shown in FIG. 1, a different display means is respectively used for the first display means and the second display means, however, it is preferable if they are unified into one display means, as shown in FIG. 2, from a viewpoint of operability and space reduction.

Further, by providing the calculating (processing) device 3 with a means 12 for writing into a storage medium, such as a floppy disk, and for reading from the storage medium, each kind of measured results can be preserved or also conveyed.

Moreover, it is possible to detect position of the pupil and further to detect the relative positions between the contact lens and a cornea or the relative positions between the pupil and the cornea, with utilizing the position detecting means according to the present invention.

Further, according to the measuring and inspecting device of the present invention, it is possible to quantitatively measure a displacement of the contact lens on the cornea. That is, in the image of the anterior eye segment displayed on the first display means, if the relationship of relative positions between the contact lens and the pupil or cornea in the case where the contact lens is moved farthest on the eye is calculated, respectively, before and after movement to be compared with each other, the displacement of the contact lens against the eye of a person who puts on the contact lens can be obtained quickly.

Further, if the measuring and inspecting device of the present invention is used, not only the position of the contact lens, but also the rotational angle of the contact lens to a specified direction on the cornea can be obtained. Especially, in the case of the toric contact lens, refractive power changes at an interval of $\pi$ as stated above, so that quantitative measurement of a position of this rotation angle is very useful.

Figure 6:
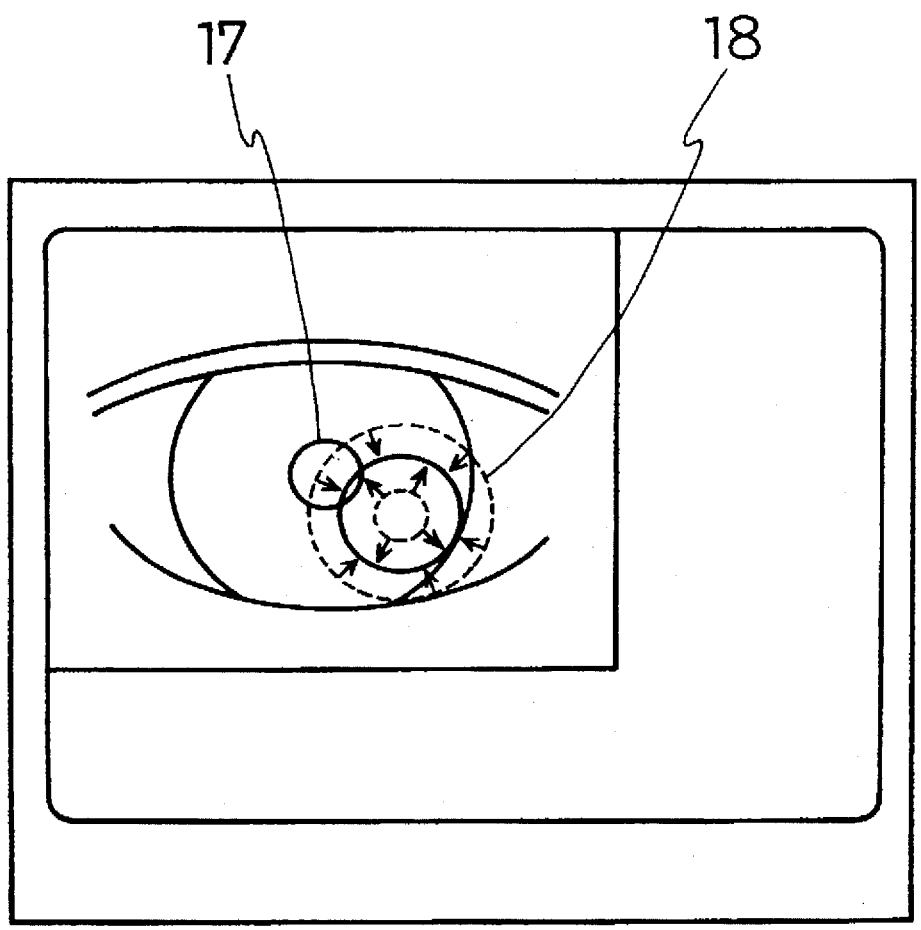
FIG. 6 is a schematic explanatory view showing an embodiment of a cursor (pointer) in the measuring and inspecting device for ophthalmologic use of the present invention.

Moreover, since it is assumed that the shape of the pupil is circular, in place of an arrow-shaped cursor (pointer) 8, as shown in FIGS. 1 to 2, a circular cursor (pointer) 18 of which the diameter is optionally changeable, as shown in FIG. 6 can also be used. Furthermore, such circular cursor (pointer) 18 is movable and changeable optionally in accordance with instruction from the operation means.

As described above, if the device of the present invention is used, and the operation is done according to the predetermined procedure, the relative positions between the pupil and the contact lens, the rotational angle, the displacement of the contact lens, and the like, can be measured quantitatively and recognized. Thus, whether or not the contact lens can provide a user with a desired optical effect can be easily judged.

Further, by combination with the illumination means capable of regulating illuminance, the design of the contact lens to which the condition for putting on must be confirmed depending on the outside condition, such as a bifocal contact lens whose plural optical power regions cover the pupil, can be done easily.

INDUSTRIAL APPLICABILITY

A measuring and inspecting device for ophthalmologic use of the present invention has the first and second position-detecting means which detect positions of the pupil and the contact lens respectively, thus, it is effectively used for precisely measuring the relationship of relative positions between the contact lens being put on and the pupil.

We claim:

1. A measuring and inspecting device for ophthalmologic use comprising:

a photographing means for photographing an anterior eye segment of a subject bearing a contact lens to be fitted; a first display means for displaying an image of the anterior eye segment of the subject and installed contact lens photographed by the photographing means; a first position-detecting means for processing the image of the anterior eye segment on said first display means to detect a position of a pupil; a second position-detecting means for processing the image of said contact lens on said first display means for detecting a position of the contact lens installed on the subject; a calculating means for calculating a relationship of relative positions between the pupil and the contact lens based on positions of the pupil and the contact lens detected by the first position-detecting means and the second position-detecting means; and a second display means for displaying the relationship of the relative position calculated by the calculating means.

2. The device of claim 1, wherein the device further includes an illuminating means for illuminating the anterior eye segment of the subject.

3. The device of claim 2, wherein the illuminating means is variable in illuminance.

4. The device of any one of claims 2 to 3, wherein the illuminating means is provided with an illuminance-measuring means.

5. The device of claim 4, wherein the first display means and the second display means are provided in a same display device.

6. The device of claim 4, wherein the second display means includes a printer means for displaying said calculated relative positions.

7. The device of any one of claims 1 to 3, wherein the first display means and the second display means are provided in a same display device.

8. The device of claim 7, wherein the second display means includes a printer means for displaying said calculated relative positions.

9. The device of any one of claim 1 to 3, wherein the second display means includes a printer means for displaying said calculated relative positions.

* * * * *